(12) United States Patent
Reiner

(10) Patent No.: US 9,931,289 B2
(45) Date of Patent: Apr. 3, 2018

(54) COSMETIC OR PHARMACEUTICAL FORMULATION

(75) Inventor: Wendy Lee Reiner, Arundel Hills (AU)

(73) Assignee: FORWARD SCOUT ENTERPRISES PTY LTD, Queensland (AU)

( * ) Notice: Subject to any disclaimer, the term of this patent is extended or adjusted under 35 U.S.C. 154(b) by 644 days.

(21) Appl. No.: 13/984,718

(22) PCT Filed: Feb. 8, 2012

(86) PCT No.: PCT/AU2012/000118
§ 371 (c)(1),
(2), (4) Date: Oct. 21, 2013

(87) PCT Pub. No.: WO2012/116391
PCT Pub. Date: Sep. 7, 2012

(65) Prior Publication Data
US 2014/0037772 A1  Feb. 6, 2014

(30) Foreign Application Priority Data
Feb. 9, 2011  (AU) ................................ 2011900419

(51) Int. Cl.
| | | |
|---|---|---|
| A61K 36/31 | (2006.01) | |
| A61K 36/13 | (2006.01) | |
| A61K 36/07 | (2006.01) | |
| A61K 36/20 | (2006.01) | |
| A61K 36/355 | (2006.01) | |
| A61K 36/60 | (2006.01) | |
| A61K 8/67 | (2006.01) | |
| A61K 31/05 | (2006.01) | |
| A61K 31/194 | (2006.01) | |
| A61K 31/728 | (2006.01) | |
| A61K 8/34 | (2006.01) | |
| A61K 8/44 | (2006.01) | |
| A61K 8/73 | (2006.01) | |
| A61Q 19/00 | (2006.01) | |
| A61Q 19/08 | (2006.01) | |
| A61K 8/92 | (2006.01) | |
| A61K 36/185 | (2006.01) | |
| A61K 36/575 | (2006.01) | |
| A61K 36/61 | (2006.01) | |
| A61K 36/71 | (2006.01) | |
| A61K 8/362 | (2006.01) | |
| A61K 8/365 | (2006.01) | |
| A61K 8/97 | (2017.01) | |
| A61K 36/23 | (2006.01) | |
| A61Q 19/10 | (2006.01) | |

(52) U.S. Cl.
CPC .............. *A61K 8/671* (2013.01); *A61K 8/347* (2013.01); *A61K 8/362* (2013.01); *A61K 8/365* (2013.01); *A61K 8/44* (2013.01); *A61K 8/735* (2013.01); *A61K 8/922* (2013.01); *A61K 8/97* (2013.01); *A61K 31/05* (2013.01); *A61K 31/194* (2013.01); *A61K 31/728* (2013.01); *A61K 36/185* (2013.01); *A61K 36/23* (2013.01); *A61K 36/575* (2013.01); *A61K 36/61* (2013.01); *A61K 36/71* (2013.01); *A61Q 19/008* (2013.01); *A61Q 19/08* (2013.01); *A61Q 19/10* (2013.01)

(58) Field of Classification Search
CPC ........ A61K 36/31; A61K 36/57; A61K 36/13; A61K 31/07; A61K 31/20; A61K 31/355; A61K 31/60; A61K 31/728
USPC ............ 424/775, 776, 769, 770, 93.51, 401, 424/9.322
See application file for complete search history.

(56) References Cited

U.S. PATENT DOCUMENTS

| | | | |
|---|---|---|---|
| 6,270,780 B1 * | 8/2001 | Carson | A61K 8/347 424/401 |
| 2003/0072777 A1 * | 4/2003 | Maes | A61K 8/41 424/401 |
| 2006/0292086 A1 * | 12/2006 | Curtis | A61K 8/046 424/47 |
| 2007/0134195 A1 * | 6/2007 | Ward | A61K 9/0014 424/74 |
| 2007/0281044 A1 * | 12/2007 | Mueller | A61K 36/185 424/727 |

(Continued)

FOREIGN PATENT DOCUMENTS

| | | | | |
|---|---|---|---|---|
| DE | 102005063063 | * | 10/2006 | ............... A61K 8/34 |
| FR | 2518402 A1 | * | 6/1983 | ............. A61K 8/922 |

(Continued)

OTHER PUBLICATIONS

Radical Skincare Maxium Poteny Eye Revive Cream, (Retrieved fom the internet), URL:? http://www.radicalskincare.com;products-eyecream.php.,published Jan. 29, 2010, 2 pgs.*
Radical Skincare Maxium Poteny Restorative Moisture, (Retrieved fom the internet), URL:? http://www.radicalskincare.com;products-eyecream.php.,published Jan. 29, 2010, 2 pgs.*
International Search Report and Written Opinion Issued by the U.S. Patent and Trademark Office as International Searching Authority for International Application No. PCT/AU2012/000118 dated May 14, 2012 (7 pgs.).

(Continued)

*Primary Examiner* — Christopher R Tate
*Assistant Examiner* — Deborah A Davis
(74) *Attorney, Agent, or Firm* — Wilmer Cutler Pickering Hale and Dorr LLP

(57) ABSTRACT

The present invention relates to a cosmetic or pharmaceutical formulation comprising a hyaluronate crosspolymer and one or more of (a) azelaic acid or an ester thereof; (b) one or more of black cumin seed oil, chaulmoogra oil, magnolia bark extract and manuka oil; and (c) resveratrol or a derivative thereof. Uses of the formulation for skin treatments, promoting collagen production and regulating cellular turnover are also described.

19 Claims, 3 Drawing Sheets

(56) References Cited

U.S. PATENT DOCUMENTS

| | | | | |
|---|---|---|---|---|
| 2008/0107758 A1* | 5/2008 | Crutchfield, III | ........ | A61K 9/12 424/732 |
| 2010/0021532 A1 | 1/2010 | Rao et al. | | |
| 2011/0268665 A1* | 11/2011 | Tamarkin | ............ | A61K 9/0014 424/43 |

FOREIGN PATENT DOCUMENTS

| | | | | | |
|---|---|---|---|---|---|
| JP | 06128251 | A | * | 5/1994 | |
| JP | 2006328048 | A | * | 12/2006 | |
| KR | 20070059121 | A | * | 6/2007 | ............. C09D 11/32 |
| WO | WO-2007009790 | A1 | | 1/2007 | |
| WO | WO-2008072905 | A1 | | 6/2008 | |
| WO | WO-2010011885 | A1 | | 1/2010 | |

OTHER PUBLICATIONS

Radical Skincare Maximum Poteny Eye Revive Cream, [Retrieved from the internet], URL: http://www.radicalskincare.com/products-eyecream.php>, published Jan. 29, 2010, 2 pgs.

Radical Skincare Maximum Poteny Restorative Moisture, [Retrieved from the internet] <URL: http://www.radicalskincare.com/products-moisturizer.php>, published May 29, 2010, 2 pgs.

* cited by examiner

COSMETIC OR PHARMACEUTICAL FORMULATION

CROSS-REFERENCE TO RELATED APPLICATIONS

This application is a U.S. national stage under 35 U.S.C. § 371 of International Application No. PCT AU2012/000118 filed on Feb. 8, 2012, which claims priority to Australian Patent Application No. 2011900419 filed on Feb. 9, 2011, the entire contents of which are hereby incorporated by reference in their entirety.

FIELD OF THE INVENTION

The present invention relates to a cosmetic or pharmaceutical formulation, to uses of the formulation in the treatment or prevention of skin conditions, and to the preparation of the formulation.

BACKGROUND OF THE INVENTION

The reference in this specification to any matter which is known, is not, and should not be taken as an acknowledgment or admission or any form of suggestion that that known matter forms part of the common general knowledge in the field of endeavour to which this specification relates.

Resveratrol and its derivatives, azelaic acid or a salt or ester thereof, and one or more of black cumin seed oil, chaulmoogra oil, magnolia bark extract and manuka oil possess a range of properties that are beneficial to the skin. For example, resveratrol and its derivatives possess antioxidant and anti-inflammatory properties and also promote collagen production. Azelaic acid or a salt or ester thereof acts to exfoliate the skin and also possesses antimicrobial properties. One or more of black cumin seed oil, chaulmoogra oil, magnolia bark extract and manuka oil possess anti-inflammatory and antibacterial properties when applied to the skin.

However, when these actives are applied to the skin in most formulations they only act for relatively short periods of time, and to provide beneficial effects for longer periods frequent application is required. Furthermore, the properties of these actives would also be beneficial to the dermis of the skin, but when applied to the skin in most formulations these actives have limited activity in the dermis.

Hyaluronate crosspolymers, such as sodium hyaluronate crosspolymer, are humectants. These crosspolymers strongly bind to water and are used to moisturize and plump the skin.

There is a need to provide a formulation that allows resveratrol and its derivatives, azelaic acid or a salt or ester thereof, or one or more of black cumin seed oil, chaulmoogra oil, magnolia bark extract and manuka oil to be delivered to the skin over a longer period of time following a single application and/or to cross the hydrolipidic film of the epidermis.

SUMMARY OF THE INVENTION

The present invention is predicated in part on the discovery that a hyaluronate crosspolymer or a salt thereof, when present in a formulation including resveratrol or a derivative thereof, azelaic acid or a salt or ester thereof, or one or more of black cumin seed oil, chaulmoogra oil, magnolia bark extract and manuka oil, allows these actives to cross the hydrolipidic film of the epidermis and/or delivers these actives to the skin over a prolonged period of time.

BRIEF DESCRIPTION OF THE FIGURES

FIG. 3 shows the effect of the WH formulation (with sodium hyaluronate crosspolymer.

DETAILED DESCRIPTION OF THE INVENTION

Figure 1:
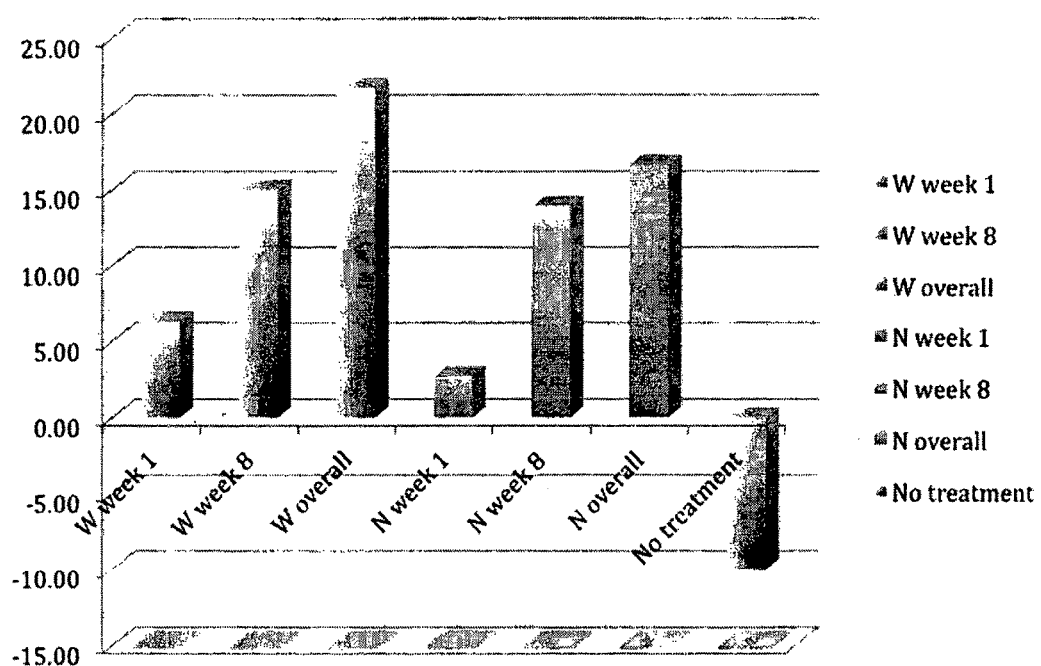
FIG. 1 shows the anti-inflammatory effect of the N (a formulation without sodium hyaluronate crosspolymer) and W (a formulation with sodium hyaluronate crosspolymer) formulations as an average percentage change in the reduction in skin responsiveness.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The term "about" is used herein to refer to conditions (e.g., amounts, concentrations, time, etc.) that vary by as much as 30%, especially by as much as 20%, and more especially by as much as 10%, 9%, 8%, 7%, 6%, 5%, 4%, 3%, 2% or 1% to a specified condition.

In one aspect of the invention, there is provided a cosmetic or pharmaceutical formulation comprising:
(i) a hyaluronate crosspolymer or a salt thereof; and
(ii) one or more of:
  (a) azelaic acid or a salt or ester thereof;
  (b) one or more of black cumin seed oil, chaulmoogra oil, magnolia bark extract and manuka oil; and
  (c) resveratrol or a derivative thereof.

In one embodiment, part (ii) of the formulation comprises one or more of:
(a) azelaic acid or a salt or ester thereof; and
(b) resveratrol or a derivative thereof.

In another embodiment, part (ii) of the formulation comprises two or more of:
(a) azelaic acid or a salt or ester thereof;
(b) one or more of black cumin seed oil, chaulmoogra oil, magnolia bark extract and manuka oil; and
(c) resveratrol or a derivative thereof.

In a further embodiment, part (ii) of the formulation comprises:
(a) azelaic acid or a salt or ester thereof; and
(b) resveratrol or a derivative thereof.

In these embodiments, part (ii) of the formulation may comprise: (a) azelaic acid or a salt or ester thereof and (b) one or more of black cumin seed oil, chaulmoogra oil, magnolia bark extract and manuka oil; or (a) azelaic acid or a salt or ester thereof and (c) resveratrol or a derivative thereof; or (b) one or more of black cumin seed oil, chaulmoogra oil, magnolia bark extract and manuka oil and (c) resveratrol or a derivative thereof.

In another embodiment, part (ii) of the formulation comprises:

(a) azelaic acid or a salt or ester thereof;
(b) one or more of black cumin seed oil, chaulmoogra oil, magnolia bark extract and manuka oil; and
(c) resveratrol or a derivative thereof.

In some embodiments the hyaluronate crosspolymer is in the form of a salt, such as a salt with sodium or potassium, especially the sodium salt. In some embodiments, the sodium hyaluronate crosspolymer is a polymer of hyaluronic acid crosslinked with a vinylsulfone, such as divinyl sulfone. A suitable sodium hyaluronate crosspolymer is Hylasome® EG10.

In some embodiments, the amount of the hyaluronate crosspolymer or a salt thereof in the formulation is less than 8% w/w; especially from 0.005% to 6% w/w; more especially from 0.05% to 4% w/w; more especially from 0.08% to 3%; most especially from 0.1 to 2% w/w.

The formulation may include azelaic acid or a salt or ester thereof. Suitable salts of azelaic acid include sodium, potassium and calcium salts, especially the sodium salt. Suitable esters of azelaic acid are especially esters that may be hydrolysed in vivo, more especially mono- and di-esters of azelaic acid with amino acids, more especially an azeloyl glycinate, most especially azeloyl diglycinate. The term "azelaic acid or a salt or ester thereof" also includes salts of esters of azelaic acid. Suitable salts of esters of azelaic acid include sodium, potassium and calcium salts, especially the potassium salt. A suitable potassium azeloyl diglycinate is Azeloglicina®.

In some embodiments, the amount of the azelaic acid or a salt or ester thereof in the formulation is less than 5% w/w; especially from 0.01% to 3% w/w; more especially from 0.05% to 2% w/w; more especially from 0.07 to 1.5% w/w; most especially from 0.1% to 1% w/w.

In various embodiments, the one or more of black cumin seed oil, chaulmoogra oil, magnolia bark extract and manuka oil is especially two or more of black cumin seed oil, chaulmoogra oil, magnolia bark extract and manuka oil; more especially three or more of black cumin seed oil, chaulmoogra oil, magnolia bark extract and manuka oil; most especially black cumin seed oil, chaulmoogra oil, magnolia bark extract and manuka oil.

In some embodiments, the one or more of black cumin seed oil, chaulmoogra oil, magnolia bark extract and manuka oil includes one or more of *Taraktogenos kurzii* seed oil, *Nigella sativa* seed oil, *Leptospermum scoparium* branch/leaf oil, potassium lauroyl wheat amino acids, palm glycerides, capryloyl glycine and *Magnolia grandiflora* bark extract. In other embodiments, the one or more of black cumin seed oil, chaulmoogra oil, magnolia bark extract and manuka oil includes one or more of thymoquinone, 5'-methoxyhydnocarpin, hydnocarpic acid, chaulmoogric acid, gorlic acid, honokiol, magnolol, flavesone, leptospermone and isoleptospermone. In various embodiments, the black cumin (*Nigella sativa*) seed oil contains thymoquinone; the chaulmoogra (*Taraktogenos kurzii*) oil contains 5'-methoxyhydnocarpin, hydnocarpic acid, gorlic acid and chaulmoogric acid; the magnolia (*Magnolia grandiflora*) bark extract contains magnolol and honokiol; and the manuka (*Leptospermum scoparium*) oil contains flavesone, leptospermone and isoleptospermone.

In one embodiment, the one or more of black cumin seed oil, chaulmoogra oil, *magnolia* bark extract and manuka oil is in the form of a composition. A suitable composition comprising black cumin seed oil, chaulmoogra oil, magnolia bark extract and manuka oil is Cutipure CLR™.

In some embodiments, the formulation comprises the composition in an amount of less than 10% w/w; especially from 0.01% to 8% w/w; more especially from 0.1% to 5% w/w; more especially from 0.2% to 4% w/w; most especially from 0.3% to 3% w/w.

In one embodiment, the amount of black cumin seed oil in the composition is from 1 to 5%. In other embodiments, the amount of chaulmoogra oil in the composition is from 10 to 25%; especially 10 to 15%. In a further embodiment, the amount of magnolia bark extract in the composition is from 0.1 to 1%. In yet a further embodiment, the amount of manuka oil in the composition is from 1 to 5%.

Resveratrol and/or derivatives of resveratrol may be present in the formulation. Derivatives of resveratrol include esters or ethers of resveratrol, especially esters or ethers that may be hydrolysed in vivo, more especially $C_1$-$C_{22}$alkyl-, $C_2$-$C_{22}$alkenyl- or $C_2$-$C_{22}$alkynyl-esters or ethers of resveratrol. Derivatives of resveratrol also include products from enzymatic treatment of resveratrol, such as fermentation products. In one embodiment, the resveratrol or a derivative thereof is a derivative of resveratrol; especially a product from an enzymatic treatment of resveratrol; more especially an extract produced by fermentation of resveratrol; most especially an extract produced by fermentation of resveratrol with *Pichia pastoris*.

A suitable extract produced by fermentation of resveratrol with *Pichia pastoris* is described in U.S. application Ser. No. 12/460,725 and WO2010/011885. In these applications a *Pichia pastoris*-resveratrol ferment extract is produced by a method comprising the steps of (i) growing the cells of *Pichia pastoris* in a media to late-logarithmic growth phase in which the carbon source in the media is exhausted, (ii) exposing the cells to a non-cytotoxic dose of resveratrol to generate new active ingredients through metabolic pathways of the yeast; and (iii) separating the new active ingredients by filtration or lysing to provide the *Pichia pastoris*-resveratrol ferment extract containing the new actives. In one embodiment the *Pichia pastoris* used is ATCC #60372. In another embodiment, fed-batch cultures are grown at 29° C. in Yeast Nitrogen-Base (YNB) growth media and supplemented with glycerol (2.7% $H_3PO_4$, 0.09% $CaSO_4$, 1.8% $K_2SO_4$, 1.5% $MgSO_4$, 0.41% KOH, 4% glycerol), the pH is kept constant at 5.0±0.5, oxygen saturation kept at 30%, the aeration rate at 1 VVM and resveratrol feed is initiated at the concentration of 0.001 mg/mL. A suitable extract produced by fermentation of resveratrol with *Pichia pastoris* is Metabiotics™ Resveratrol.

In some embodiments, the amount of resveratrol or a derivative thereof in the formulation is less than 5% w/w; especially from 0.01% to 3% w/w; more especially from 0.5% to 2% w/w; more especially from 0.7% to 1.5% w/w; most especially about 1% w/w.

In some embodiments, the formulation further comprises one or more agents that stimulate collagen production. The one or more agents that stimulate collagen production may be selected from one or more of: a retinoid, an isoflavone or a substituted derivative thereof and salicylic acid or a salt or derivative thereof.

In one embodiment, the agent that stimulates collagen production is a retinoid. The term "retinoid", as used herein, includes retinol, retinoic acid; derivatives of retinol, derivatives of retinoic acid, and salts of retinoic acid. Derivatives of retinol include esters or ethers, especially esters or ethers that may be hydrolysed in vivo, more especially $C_1$-$C_{22}$alkyl-, $C_2$-$C_{22}$alkenyl- or $C_2$-$C_{22}$alkynyl-esters or ethers. Derivatives of retinoic acid include esters, especially esters that may be hydrolysed in vivo, more especially $C_1$-$C_{22}$alkyl-, $C_2$-$C_{22}$alkenyl- or $C_2$-$C_{22}$alkynyl-esters. In one embodiment, the retinoid is retinol or a derivative thereof, such as retinol palmitate; more especially retinol. In another embodiment, the retinol is all-trans-retinol.

In one embodiment, the amount of the retinoid in the formulation is less than 0.1% w/w; especially less than 0.05% w/w; more especially less than 0.03% w/w; more especially less than 0.02% w/w; more especially from 0.005 to 0.02% w/w; most especially from 0.01 to 0.02% w/w.

In another embodiment, the agent that stimulates collagen production is an isoflavone or a substituted derivative thereof. In one embodiment, the isoflavone is substituted with one or more groups selected from hydroxy, halo, $R_1$—, $R_1$—O—$(CH_2)_q$—, $R_1$—S—$(CH_2)_q$—, $R_1$—CO—$(CH_2)_q$—, $R_1$—CO—O—$(CH_2)_q$— and $R_1$—O—CO—$(CH_2)_q$—; wherein $R_1$ is selected from alkyl, alkenyl, alkynyl, aryl, heteroaryl, heterocyclyl, cycloalkyl and cycloalkenyl; and q is an integer from 0 to 6. Two or more substituents on the isoflavone ring may also be linked to form an aryl or heteroaryl ring. The alkyl, alkenyl, alkynyl, aryl, heteroaryl, heterocyclyl, cycloalkyl and cycloalkenyl substituents may also be further substituted, for example with one or more of hydroxy, halo, alkyl, alkenyl, alkynyl, alkyl-O—, alkenyl-O—, alkynyl-O—, aryl, heteroaryl, heterocyclyl, cycloalkyl and cycloalkenyl groups. In one embodiment the substituted derivative of isoflavone is substituted with one or more groups selected from hydroxy, alkyl-O, alkyl, alkenyl and heterocyclyl-O—, or two or more substituents on the isoflavone ring are linked to form an aryl or heteroaryl ring. In a further embodiment, the isoflavone is substituted with one or more hydroxy groups.

In one embodiment, the isoflavone or a substituted derivative thereof is a soy isoflavone; more especially genistein or daidzein; most especially genistein.

In one embodiment, the amount of isoflavone or a substituted derivative thereof in the formulation is less than 0.1% w/w; more especially less than 0.05% w/w; more especially less than 0.01% w/w; more especially less than 0.005% w/w; most especially from 0.001 to 0.005% w/w.

In a further embodiment, the agent that stimulates collagen production is salicylic acid or a salt or derivative thereof. Derivatives of salicylic acid include ethers and esters of salicylic acid, especially esters or ethers that may be hydrolysed in vivo, more especially $C_1$-$C_{22}$alkyl-, $C_2$-$C_{22}$alkenyl- or $C_2$-$C_{22}$alkynyl-esters or ethers. The agent that stimulates collagen production may be salicylic acid or a salt thereof, especially salicylic acid.

In one embodiment, the amount of salicylic acid or a salt or derivative thereof in the formulation is less than 6% w/w; especially less than 4% w/w; more especially from 0.1% to 4% w/w; more especially from 0.5% to 3% w/w; more especially from 0.7% to 2% w/w; more especially from 1% to 2% w/w.

Many pharmaceutical and cosmetic formulations use an alpha hydroxy acid rather than a beta hydroxy acid (such as salicylic acid) to stimulate collagen production. However, to penetrate the dermis the alpha hydroxy acid must be present in 10% or greater of a formulation. It is believed that when such formulations are used over prolonged periods, alpha hydroxy acids may cause dryness, itchiness and light sensitivity to acne prone and sensitive skin. Salicylic acid generally possesses superior exfoliation and anti-inflammatory properties compared to alpha hydroxy acids. Without wishing to be bound by theory, it believed that the combination of salicylic acid and a hyaluronate crosspolymer or a salt thereof advantageously allows salicylic acid to be used at low concentrations in the formulation, which causes less skin irritation than the use of alpha hydroxy acids.

In some embodiments, the formulation further comprises one or more antioxidants. In one embodiment, the one or more antioxidants are selected from: ascorbic acid or a salt or derivative thereof, tocopherol or a derivative thereof, ubiquinone or a derivative thereof, lactobionic acid or a salt or derivative thereof, gluconolactone or derivative thereof and maltobionic acid or a salt or derivative thereof.

In one embodiment, the antioxidant is one or more of ascorbic acid or a salt or derivative thereof. Derivatives of ascorbic acid include ethers and esters of ascorbic acid. In one embodiment, an ether or ester of ascorbic acid is an ester or ether that may be hydrolysed in vivo. The ether and ester of ascorbic acid may be a phosphate ether of ascorbic acid; a sulphate ether of ascorbic acid; a mono-, di-, tri- or tetra-$C_1$-$C_{22}$alkyl-, $C_2$-$C_{22}$alkenyl- or $C_2$-$C_{22}$alkynyl ether of ascorbic acid (especially a $C_8$-$C_{22}$alkyl or $C_8$-$C_{22}$alkenyl ether); or a mono-, di-, tri- or tetra-$C_1$-$C_{22}$alkyl-, $C_2$-$C_{22}$alkenyl- or $C_2$-$C_{22}$alkynyl ester of ascorbic acid (especially a $C_8$-$C_{22}$alkyl or $C_8$-$C_{22}$alkenyl ester). Examples of derivatives of ascorbic acid include an ascorbyl phosphate; an ascorbyl sulphate; and a mono-, di-, tri- or tetra-$C_{16}$-$C_{18}$alkyl ester of ascorbic acid, such as an ascorbyl palmitate, an ascorbyl dipalmitate, an ascorbyl tetraisopalmitate and an ascorbyl stearate. In one embodiment, the one or more of ascorbic acid or a salt or derivative thereof is selected from one or more of ascorbic acid, an ascorbyl phosphate and a mono-, di-, tri- or tetra-$C_{16}$-$C_{18}$alkyl ether of ascorbic acid or a salt thereof; more especially selected from one or more of a salt of ascorbic acid, a salt of ascorbyl phosphate and a tetra-$C_{16}$-$C_{18}$alkyl ester of ascorbic acid; most especially selected from one or more of sodium ascorbate, sodium ascorbyl phosphate, ascorbyl phosphate and ascorbyl tetraisopalmitate.

In one embodiment, the amount of one or more of ascorbic acid or a salt or derivative thereof in the formulation is less than 9% w/w; especially less than 6% w/w; more especially less than 4% w/w; more especially less than 3.5% w/w; more especially from 0.001 to 3.5% w/w; most especially from 0.01 to 3.1% w/w.

In another embodiment, the antioxidant is one or more of tocopherol or a derivative thereof. Derivatives of tocopherol include tocotrienols and ethers and esters of tocopherol, such as ethers and esters of tocopherol that may be hydrolysed in vivo. In one embodiment, a derivative of tocopherol is a $C_1$-$C_{22}$alkyl-, $C_2$-$C_{22}$alkenyl- or $C_2$-$C_{22}$alkynyl ester or a $C_1$-$C_{22}$alkyl-, $C_2$-$C_{22}$alkenyl- or $C_2$-$C_{22}$alkynyl ether, for example tocopherol acetate or tocopherol stearate. In one embodiment, the one or more of tocopherol or a derivative thereof is selected from one or more of tocopherol and an ester of tocopherol; especially one or more of tocopherol and tocopherol acetate.

In one embodiment, the amount of one or more of tocopherol or a derivative thereof in the formulation is less than 0.1% w/w; more especially less than 0.05% w/w; more especially less than 0.03% w/w; more especially less than 0.02% w/w; more especially from 0.005% w/w to 0.02% w/w; most especially about 0.013%.

In a further embodiment, the antioxidant is ubiquinone or a derivative thereof. Derivatives of ubiquinone include compounds of the formula

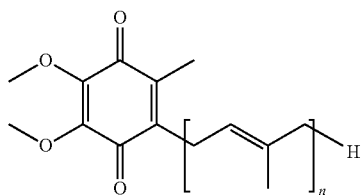

wherein n is an integer from 6 to 9. For ubiquinone, n is 10. In one embodiment, the ubiquinone or a derivative thereof is ubiquinone. In one embodiment, the amount of the ubiquinone or a derivative thereof in the formulation is less than 0.01% w/w; more especially less than 0.005% w/w; most especially less than 0.003% w/w.

In another embodiment, the antioxidant is one or more of lactobionic acid or a salt or derivative thereof; gluconolactone or derivative thereof; and maltobionic acid or a salt or derivative thereof. Derivatives of lactobionic acid, gluconolactone and maltobionic acid include ethers and esters, such as mono-, di- or tri-$C_1$-$C_{22}$alkyl-, $C_2$-$C_{22}$alkenyl- or $C_2$-$C_{22}$alkynyl ethers and mono-, di- or tri-$C_8$-$C_{22}$alkyl-, $C_2$-$C_{22}$alkenyl- or $C_2$-$C_{22}$alkynyl esters and combinations thereof. In one embodiment, the antioxidant is one or more of lactobionic acid or a salt thereof, gluconolactone, and maltobionic acid or a salt thereof; especially one or more of lactobionic acid or a salt thereof and gluconolactone; most especially one or more of lactobionic acid and gluconolactone.

Unless otherwise stated, suitable salts of ingredients in the formulation include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benzenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

As used herein, the term "halo" refers to fluoro, chloro, bromo and iodo.

As used herein, the term "alkyl" refers to a straight chain or branched saturated hydrocarbon group having 1 to 22 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, heptyl, octyl, nonyl, lauryl, myristyl, palmityl, stearyl and arachidyl.

As used herein, the term "alkenyl" refers to a straight-chain or branched hydrocarbon group having one or more double bonds between carbon atoms and having 2 to 22 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl, decenyl, undecenyl, dodecenyl, tetradecenyl, hexadecenyl, octadecenyl, eicosatetraenyl and docosenyl.

As used herein, the term "alkynyl" refers to a straight-chain or branched hydrocarbon group having one or more triple bonds between carbon atoms and having 2 to 22 carbon atoms. Where appropriate, the alkynyl group may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to, ethynyl, propynyl, butynyl, pentynyl, hexynyl, octynyl, nonynyl, decynyl, undecynyl and dodecynyl.

As used herein, the term "cycloalkyl" refers to a saturated cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentanyl, cyclohexanyl and cycloheptanyl.

As used herein, the term "cycloalkenyl" refers to a cyclic hydrocarbon having at least one double bond, which is not aromatic. The cycloalkenyl ring may include a specified number of carbon atoms. For example, a 4 to 8 membered cycloalkenyl group contains at least one double bond and 4, 5, 6, 7 or 8 carbon atoms. Examples of suitable cycloalkenyl groups include, but are not limited to cyclopentenyl, cyclopenta-1,3-dienyl, cyclohexenyl, cyclohexen-1,3-dienyl and cyclohexen-1,4-dienyl.

As used herein, the term "aryl" is intended to mean any stable, monocyclic, bicyclic or tricyclic carbon ring of up to 7 atoms in each ring, wherein at least one ring is aromatic. When more than one ring is present, the rings may be fused to one another. Examples of aryl groups include, but are not limited to, phenyl, naphthyl, tetrahydronaphthyl, indanyl, biphenyl, binaphthyl, anthracenyl, phenanthrenyl, phenalenyl and fluorenyl.

The term "heterocyclyl" as used herein, refers to a cycloalkyl or cycloalkenyl group in which one or more carbon atoms have been replaced by heteroatoms independently selected from N, S and O. For example, between 1 and 4 carbon atoms in each ring may be replaced by heteroatoms independently selected from N, S and O. If the heterocyclyl group includes more than one ring in a ring system, at least one ring is heterocyclic. Examples of suitable heterocyclyl groups include tetrahydrofuranyl, tetrahydrothiophenyl, pyrrolidinyl, pyrrolinyl, dithiolyl, 1,3-dioxolanyl, pyrazolinyl, imidazolinyl, imidazolidonyl, dioxanyl, dioxinyl, piperidinyl, piperazinyl, morpholinyl, thiomorpholinyl, pyranyl, dithianyl, and tetrahydropyranyl.

The term "heteroaryl" as used herein, represents a stable monocyclic, bicyclic or tricyclic ring of up to 7 atoms in each ring, wherein at least one ring is aromatic and at least one ring contains from 1 to 4 heteroatoms selected from the group consisting of O, N and S. When more than one ring is present the rings may be fused. Examples of suitable heteroaryl groups include pyrrolyl, furanyl, thienyl, pyrazolyl, imidazolyl, triazolyl, isoxazolyl, oxazolyl, thiazolyl, isothiazolyl, oxadiazolyl, oxatriazolyl, pyridinyl, pyridazinyl, pyrimidinyl, pyrazinyl, triazinyl, azepinyl, oxepinyl, thiepinyl, diazepinyl, coumaranyl, benzofuranyl, isobenzofuranyl, benzothienyl, indolyl, indolinyl, isoindolyl, benzimidazolyl, benzisoxazolyl, benzoxazolyl, benzothiazolyl, benzopyranyl, quinolinyl, tetrahydroquinolinyl, isoquinolinyl, quinazolinyl, quinoxalinyl and tetrahydroquinoxalinyl.

In various embodiments, the formulation may be in the form of a lotion, a cream, a water-in-oil emulsion, an oil-in-water emulsion, a suspension, an ointment, a gel, a paste or another form that would be suitable for administration to the skin of the user. In other embodiments, the formulation may be used as a cleanser, a face wash, a serum, an active gel, a day cream, a day moisturizer, a night cream, a toner, a face sunscreen or a body sunscreen.

The formulation may also further include one or more chelating agents; especially one or more chelating agents selected from ethylenediamine tetraacetic acid (EDTA), diethylene triamine pentaacetic acid (DTPA), hexamethyenediamine tetraacetic acid, ethylenediamine tetra(methylenephosphonic acid), diethylenetriamine penta(methylenephosphonic acid), hexamethylenediamine tetra(ethylene phosphonic acid) and salts thereof; more especially ethylenediamine tetraacetic acid (EDTA) and salts thereof; most especially disodium ethylenediamine tetraacetic acid (EDTA). In one embodiment, the amount of chelating agent in the formulation is less than 2% w/w; especially 0.005 to w/w; more especially 0.005 to 0.5% w/w; most especially 0.01 to 0.2% w/w.

The formulation may also further include one or more preservative agents; especially one or more preservative agents selected from phenoxyethanol, ethylhexylglycerin, benzyl alcohol, salicylic acid, glycerin and sorbic acid; more especially two or more preservative agents selected from phenoxyethanol, ethylhexylglycerin, benzyl alcohol, salicylic acid, glycerin and sorbic acid; most especially a combination of phenoxyethanol and ethylhexylglycerin (such as Euxyl® PE 9010) or a combination of benzyl alcohol, salicylic acid, glycerin and sorbic acid (such as Mikrokill® ECT). In one embodiment, the amount of preservative agents in the formulation is less than 5% w/w; especially less than 3% w/w; more especially less than 2% w/w; most especially less than 1.2% w/w.

The formulation may also further include one or more exfoliants; especially an organic powder or wax microspheres. The wax microspheres are especially microspheres of jojoba esters, rice bran wax or carnauba wax; more especially microspheres of jojoba esters. In one embodiment the microspheres are in a size range of 150 to 600 microns, more especially 250 to 600 microns. Suitable microspheres of jojoba esters are Florabeads® Maize.

The organic powder is especially an organic powder selected from polyamide powder, polyester powder, polyethylene powder, polypropylene powder, polystyrene powder, polyurethane powder, benzoguanamine powder, polymethylbenzoguanamine powder, polytetrafluoroethylene powder, poly(methyl methacrylate) powder, cellulose powder, silk powder, nylon powder such as Nylon 12 and Nylon 6, acrylic powder, acrylic elastomer, styrene/acrylic acid copolymer, divinylbenzene/styrene copolymer, vinyl resin, urea resin, phenol resin, fluororesin, silicone resin, acrylic resin, melamine resin, epoxy resin, polycarbonate resin, microcrystalline fibre powder, starch powder, and lauroyl lysine; more especially selected from polyethylene powder, cellulose powder, silk powder, nylon powder, polystyrene powder, poly(methyl methacrylate) powder and polypropylene powder; most especially polyethylene powder.

In one embodiment, the amount of exfoliant in the formulation is less than 10% w/w; especially less than 7% w/w; more especially less than 5% w/w; more especially from 2 to 5% w/w; most especially about 3% w/w.

The formulation may also include a humectant; especially a humectant selected from 1,2-pentanediol, 1,2-hexanediol, 1,2-heptanediol, polyethylene glycol, propylene glycol, dipropylene glycol, 1,3-butylene glycol, hexylene glycol, glycerin, diglycerin and sorbitol; most especially glycerin. In one embodiment, the amount of humectant in the formulation is less than 30% w/w; especially less than 20% w/w; more especially from 2% to 15% w/w; more especially from 2% to 12% w/w; most especially from 4% to 11% w/w.

In another embodiment, the formulation further includes an emollient; especially an emollient fatty acid ester; more especially the emollient is selected from $C_{12}$-$C_{15}$ alkyl benzoate, butyl stearate, cetearyl ethylhexanoate and isopropyl myristate, cetyl palmitate, diisopropyl adipate, diethylhexyl adipate, caprylic/capric triglyceride, isocetyl stearate, isopropyl myristate, isopropyl palmitate, lauryl lactate, myristyl lactate, myristyl myristate, ethylhexyl cocoate, ethylhexyl hydroxystearate, ethylhexyl palmitate, ethylhexyl pelargonate, ethylhexyl stearate, diethylhexyl succinate, propylene glycol, dicaprylate/dicaprate, PPG-2 myristyl ether propionate, pentaerythrityl, tetracaprylate/caprate, pentaerythrityl tetraisostearate, cetyl esters, isotridecyl isononanoate, and stearyl heptanoate and stearyl caprylate; more especially the emollient is selected from cetearyl ethylhexanoate and isopropyl myristate, isopropyl myristate, isopropyl palmitate, diisopropyl adipate, myristyl lactate and ethylhexyl pelargonate; most especially the emollient is diisopropyl adipate or isopropyl myristate. A suitable isopropyl myristate is Crodamol™ IPM-LQ-(SG). In one embodiment, the amount of emollient in the formulation is less than 15% w/w; especially less than 10% w/w; more especially from 0.25% to 8% w/w; most especially from 1% to 6% w/w.

The formulation may also further include one or more silicon materials; especially one or more silicon based organic polymers; more especially one or more of dimethicone and a dimethicone crosspolymer; most especially one or more of dimethicone and a crosspolymer of cyclopentasiloxane and dimethicone. A suitable dimethicone is Dow Corning® 200 Fluid 350 CST, and a suitable crosspolymer of cyclopentasiloxane and dimethicone is Dow Corning® 9040 Silicone Elastomer Blend. The amount of silicon material in the formulation may be less than 15% w/w; more especially less than 12% w/w; more especially from 1% to 10% w/w; most especially from 3% to 7% w/w.

In a further embodiment, the formulation further includes a pH adjuster; more especially the pH adjuster is selected from a hydroxide salt, an amine, an inorganic acid or a carboxylic acid; more especially the pH adjuster is selected from sodium hydroxide, ammonium hydroxide, potassium hydroxide, ethanolamine, diethanolamine, triethanolamine, diisopropanolamine, aminomethylpropanol, tris(hydroxymethyl)aminomethane (tromethamine), hydrochloric acid, nitric acid, sulphuric acid, acetic acid and lactic acid; most especially the pH adjuster is selected from sodium hydroxide and lactic acid.

In one embodiment, the pH of the formulation is from 4.0 to 9.0; especially from 4.0 to 8.0; more especially from 4.5 to 8.0; more especially from 5.0 to 7.5; most especially from 5.0 to 6.0, from 5.5 to 6.5, or from 6.5 to 7.5.

The formulation may also include one or more thickeners; more especially one or more thickeners selected from gum Arabic, tragacanth gum, arabinogalactan, locust bean gum (carob gum), guar gum, karaya gum, carrageenan, pectin, agar-agar, quince seed, starch from rice, corn, potato or wheat, algae colloid, trant gum, xanthan gum, dextran, succinoglucan, pullulan, collagen, casein, albumin, gelatine, carboxymethyl starch, methylhydroxypropyl starch, methyl cellulose, ethyl cellulose, methylhydroxypropyl cellulose, carboxymethyl cellulose, hydroxymethyl cellulose, hydroxypropyl cellulose, nitrocellulose, sodium cellulose sulphate, sodium carboxymethyl cellulose, crystalline cellulose, cellulose powder, sodium alginate, propylene glycol alginate, polyvinyl methylether, polyvinylpyrrolidone, carboxyvinyl polymer, polyethylene glycol, polyoxyethylene/polyoxypropylene copolymer, a cross-linked polyacrylate polymer, sodium polyacrylate, polyethyl acrylate, polyacrylamide, polyethyleneimine, cationic polymers, bentonite, aluminum magnesium silicate, laponite, smectite, saponite, hectorite, and silicic anhydride; more especially one or more thickeners selected from gum Arabic, tragacanth gum, arabinogalactan, locust bean gum (carob gum), guar gum, karaya gum, carrageenan, pectin, agar-agar, quince seed, starch from rice, corn, potato or wheat, algae colloid, trant gum, xanthan gum, dextran, succinoglucan, pullulan, and a cross-linked polyacrylate polymer; most especially one or more thickeners selected from xanthan gum, carrageenan and cross-linked polyacrylate polymers described under the International Nomenclature for Cosmetic Ingredients (INCI) as Carbomer (especially cross-linked polyacrylate polymers which in a 0.5% aqueous solution which has been neutralised with a base possess a viscosity of between 40,000 and 65,000 mPa·s at 20 rpm and 25° C., such as Carbopol® 940, Carbopol® 980, Carbopol® Ultrez 10 polymer and Carbopol® Ultrez 21 polymer, especially Carbopol® 940). A suitable xanthan gum is Xanthan 200, and a suitable carrageenan is Carrageenan Lambda. In one embodiment, the amount of thickener in the formulation is less than 5% w/w; especially less than 3% w/w; more especially from 0.1% to 2.5% w/w; more especially from 0.2% to 1.8% w/w; most especially from 0.4% to 1.4% w/w.

The formulation may also include one or more sunscreen active agents; especially salicylic acid and salts thereof (such as potassium, sodium and triethanolamine salts), 4-methylbenzylidene camphor (3-(4-methylbenzylidene)-d-1 camphor), aminobenzoic acid (4-aminobenzoic acid; PABA), bemotrizinol (Tinosorb® S), benzophenone (phenylketone), benzophenone-2 (bis(2,4-dihydroxyphenyl) methanone), benzylidene camphor sulfonic acid (alpha-(2-oxoborn-3-ylidene)toluene-4-sulphonic acid and its salts), butyl methoxy dibenzoylmethane (1-(4 tert butylphenyl)-3 (4-methoxyphenyl)propane-1,3-dione; avobenzone; BMDM; 4-tert-butyl-4-methoxy dibenzoylmethane), camphor benzalkonium methosulfate (N,N,N-trimethyl-4-(oxoborn-3-ylidenemethyl)anilinium methyl sulfate), cinoxate, diethylamino hydroxybenzoyl hexyl benzoate (benzoic acid 2-[4-(diethylamino)-2-hydroxybenzoyl] hexyl ester; Uvinul® A Plus), disodium phenyl dibenzimidazole tetrasulfonate (Neo Heliopan®), dioxybenzone (benzophenone 8), drometrizole trisiloxane (phenol 2-(2H-benzotriazol-2-yl)-4-methyl-6-[2-methyl-3-[1,3,3,3-tetramethyl-1-[(trimethylsilyl)oxy]disiloxanyl]propyl; Mexoryl™ XL), ecamsule (terephthalylidene dicamphor sulfonic acid), homosalate (homomethyl salicylate), isoamyl methoxycinnamate (isopentenyl-4-methoxycinnamate (isoamyl 4-methoxycinnamate)), isopropylbenzyl salicylate (4-isopropylbenzyl salicylate), menthyl anthranilate (methyl 2-aminobenzoate), methylene bis-benzotriazolyl tetramethylbutyl phenol (2,2'-methylene-bis-6-(2H-benzotriazol-2-yl)-4-(tetramethylbutyl)-1,1,3,3-phenol; Tinosorb® M), octocrylene (2-cyano-3,3-diphenyl acrylic acid 2-ethyl hexyl ester; 2-ethylhexyl-2-cyano-3,3 diphenylacrylate), octyl methoxcinnamate (ethylhexyl methoxycinnamate), octyl salicylate (2-ethylhexyl salicylate), octyl triazone (2,4,6-trianalino-(p-carbo-2'-ethylhexyl-1'oxy)-1,3,5-triazine); oxybenzone (benzophenone 3), padimate O (2-ethylhexyl 4-dimethylaminobenzoate; octyl dimethyl PABA), PEG-25 PABA (ethoxylated ethyl 4-aminobenzoic acid; PEG25 PABA), phenylbenzimidazole sulfonic acid (2-phenylbenzimidazole-5-sulfonic acid and its potassium, sodium and triethanolamine salts), polysilicone-15 (dimethicodiethylbenzalmalonate; Parsol® SLX), sulisobenzone (benzophenone 4), sulisobenzone sodium (benzophenone 5), titanium dioxide, triethanolamine salicylate (trolamine salicylate), zinc oxide, benzophenone-9 (sodium dihydroxy dimethoxy disulfobenzophenone); iscotrizinol (diethylhexyl butamido triazone; DBT); especially titanium dioxide and zinc oxide.

The formulation may also further include one or more surfactants; especially one or more surfactants selected from the group consisting of an anionic surfactant, a cationic surfactant, an amphoteric surfactant, and a non-ionic surfactant.

The anionic surfactant may be selected from an alkylamido carboxylic acid and an alkyl carboxylic acid and salts thereof (such as sodium, magnesium, ammonium and mono-, di- and triethanolamine salts thereof); more especially the anionic surfactant may be selected from a $C_8$-$C_{22}$alkylamido carboxylic acid, a $C_8$-$C_{22}$alkyl carboxylic acid and salts thereof; more especially the anionic surfactant may be selected from an N—$C_8$-$C_{22}$alkoyl sarcosinate, an N—$C_8$-$C_{22}$alkoxy glutamate, a $C_8$-$C_{22}$alkylcarboxylic acid and salts thereof; more especially the anionic surfactant may be selected from lauroyl sarcosinate, stearoyl glutamate, stearic acid and salts thereof, polyhydroxystearic acid and salts thereof, and isostearic acid and salts thereof; most especially the anionic surfactant may be selected from sodium lauroyl sarcosinate, sodium stearoyl glutamate, stearic acid, polyhydroxystearic acid and isostearic acid.

The cationic surfactant may be a quarternary salt of an alkyl and/or acyl amine; especially salts of diethanolamine, triethanolamine, tetraethanolamine, arginine and lysine.

The amphoteric surfactant may be an alkyl amido alkyl betaine; more especially an alkyl amidopropyl betaine; more especially a $C_8$-$C_{18}$alkyl amidopropyl betaine; more especially a $C_{11}/_{17}$alkyl amidopropyl betaine. A suitable $C_{11}/_{17}$alkyl amidopropyl betaine is Genagen® CAB.

The non-ionic surfactant may be selected from one or more of a fatty alcohol, a sugar alkylether, a polyoxyethylenated fatty alcohol ether, a polyoxyethylenated sorbitan derivative, lecithin or a derivative thereof, and a glycerin fatty acid ester; more especially the non-ionic surfactant may be selected from one or more of a $C_8$-$C_{22}$alkyl alcohol, a $C_8$-$C_{22}$alkyl glucoside, a polyoxyethylenated $C_8$-$C_{22}$alkylether comprising 1 to 100 oxyethylenated groups, a polyoxyethylenated sorbitan mono $C_8$-$C_{22}$alkylether comprising 1 to 100 oxyethylenated groups, lecithin and a tri-$C_8$-$C_{22}$alkyl glyceride; more especially the non-ionic surfactant may be selected from one or more of cetearyl alcohol, cetearyl glucoside, ceteareth-20, polyoxyethylene 20 sorbitan monolaurate (polysorbate 20), polyoxyethylene 20 sorbitan monooleate (polysorbate 80), lecithin and a caprylic/capric triglyceride. Suitable non-ionic surfactants include Cosmowax D and Emulgade® PL68/50.

In one embodiment, the amount of surfactant in the formulation is less than 50% w/w; especially less than 40% w/w; more especially, less than 30% w/w; more especially from 0.1% to 12% w/w or from 15% to 30% w/w; more especially from 0.5% to 10% w/w or from 17% to 25% w/w; most especially from 0.8% to 8% w/w or from 20 to 25% w/w.

The formulation may further include solvents such as water, an alcohol or an oil. In one embodiment, the formulation includes water in an amount of less than 95% w/w;

especially from 20% to 95% w/w; more especially from 30% to 95% w/w; most especially from 40% to 90% w/w.

Other ingredients, such as fragrances and colouring may also be added to the formulation.

The relative proportion of various ingredients in the formulation depends upon the intended use of the formulation. For example, a face wash, which is intended to clean the skin, may have a higher proportion of surfactants than a serum or a night cream. The pH may also vary depending on the intended use of the formulation.

In another aspect of the invention, there is provided a method of treating or preenting one or more of a condition involving blocked sebaceous glands, an inflammatory skin condition, a microbial skin infection, dermal oxidation damage, and pigmentation, especially an inflammatory skin condition, comprising administering to a subject in need thereof the cosmetic or pharmaceutical formulation.

In a further aspect of the invention, there is provided a method of promoting collagen production in a dermal matrix or regulating cellular turnover, comprising administering to a subject in need thereof the cosmetic or pharmaceutical formulation.

In a further aspect of the invention, there is provided a method of treating a bacterial infection, comprising administering to the skin of a subject in need thereof the cosmetic or pharmaceutical formulation.

In another aspect of the invention, there is provided a use of
(i) a hyaluronate crosspolymer or a salt thereof; and
(ii) one or more of:
  (a) azelaic acid or a salt or ester thereof;
  (b) one or more of black cumin seed oil, chaulmoogra oil, magnolia bark extract and manuka oil; and
  (c) resveratrol or a derivative thereof
in the manufacture of a cosmetic or pharmaceutical formulation for the treatment or prevention of one or more of a condition involving blocked sebaceous glands, an inflammatory skin condition, a microbial skin infection, dermal oxidation damage and pigmentation, especially an inflammatory skin condition.

In another aspect of the invention, there is provided a use of
(i) a hyaluronate crosspolymer or a salt thereof; and
(ii) one or more of:
  (a) azelaic acid or a salt or ester thereof;
  (b) one or more of black cumin seed oil, chaulmoogra oil, magnolia bark extract and manuka oil; and
  (c) resveratrol or a derivative thereof
in the manufacture of a cosmetic or pharmaceutical formulation for the promotion of collagen production in a dermal matrix or the regulation of cellular turnover.

In another aspect of the invention, there is provided a use of
(i) a hyaluronate crosspolymer or a salt thereof; and
(ii) one or more of:
  (a) azelaic acid or a salt or ester thereof;
  (b) one or more of black cumin seed oil, chaulmoogra oil, magnolia bark extract and manuka oil; and
  (c) resveratrol or a derivative thereof
in the manufacture of a cosmetic or pharmaceutical formulation for treatment of a bacterial infection.

In one embodiment, the condition involving blocked sebaceous glands includes one or more of comedones, pustules, pimples and cysts.

In one embodiment, the inflammatory skin condition is rosacea, sunburn or dermatitis.

In another embodiment, the microbial skin infection is acne.

The formulation may also be useful for plumping the skin, hydrating the skin and smoothing out wrinkles.

The formulation may be prepared by blending methods as known in the art. Suitable exemplary methods for preparing the formulations are set out below.

The formulation may be prepared by combining water, chelants, and preservatives and heating to 75° C. Following this, thickeners are added and stirring is continued until the ingredients are hydrated. A blend of surfactants, silicon materials and emollients at 75° C. is then added to the water/chelant/preservative/thickener mixture. After blending this mixture together, the mixture is cooled to 35° C. under constant low shear. To this mixture is then added the hyaluronate crosspolymer or a salt thereof, one or more of black cumin seed oil, chaulmoogra oil, magnolia bark extract and manuka oil, azelaic acid or a salt or ester thereof, resveratrol or a derivative thereof, agents that stimulate collagen production and antioxidants. A homogenous mixture of water, humectants, salicylic acid or a salt or derivative thereof and ascorbic acid or a salt or derivative thereof is then added to the mixture under constant low shear. The pH of the formulation is then adjusted to between 5.5 and 6.5 before use.

Another preparation of the formulation is to combine water, preservatives and chelants, before adding thickeners. This mixture is stirred until well combined. To this mixture is added a slurry of humectants, the hyaluronate crosspolymer or a salt thereof, azelaic acid or a salt or ester thereof, resveratrol or a derivative thereof and agents that stimulate collagen production. Sodium hydroxide is then added to the mixture, before addition of a blend of one or more of black cumin seed oil, chaulmoogra oil, magnolia bark extract and manuka oil, and surfactants. After stirring until the mixture is homogenous, the pH of the mixture is adjusted to a pH between 5.0 and 6.0.

A further preparation of the formulation is to combine water and preservatives stir the mixture until combined, heating to 75° C. To this is added a blend of humectants and thickeners, and the resultant mixture is stirred at 75° C. A blend of emollients, surfactants and silicon material is prepared at 75° C., and this blend is added to the water/preservative/humectant/thickener mixture. After the mixture emulsifies, it is cooled to 35° C. under constant low shear. To this mixture is then added a blend of humectants, antioxidants, one or more of black cumin seed oil, chaulmoogra oil, magnolia bark extract and manuka oil, the hyaluronate crosspolymer or a salt thereof, azelaic acid or a salt or ester thereof, resveratrol or a derivative thereof and agents that stimulate collagen production. After the mixture is stirred until homogenous the pH is adjusted to between 5.5 and 6.5.

A further preparation of the formulation is to prepare a mixture of water, humectants, preservatives and thickeners at 75° C. and add to this a pre-prepared blend of sunscreen active, agents, emollients, surfactants and silicon material at 75° C. After emulsification, the mixture is allowed to cool to 35° C. before adding one or more of black cumin seed oil, chaulmoogra oil, magnolia bark extract and manuka oil, the hyaluronate crosspolymer or a salt thereof, resveratrol or a derivative thereof and antioxidants. The mixture is then stirred until homogenous and then the pH adjusted to between 6.5 and 7.5 before use.

Another preparation is to combine water, preservatives and chelants and stir until combined. Following this, surfactants are added. A slurry of humectants and thickeners is then added to the mixture, which is then stirred until thoroughly hydrated. To this mixture is then added a pre-prepared paste of humectants, organic powder, agents that stimulate collagen production, microspheres for exfoliation, the hyaluronate crosspolymer or a salt thereof, antioxidants and azelaic acid or a salt or ester thereof. This mixture is then stirred until homogenous before adjusting the pH to between 5.5 and 6.5.

The invention will now be described with reference to the following Examples which illustrate some aspects of the present invention. However, it is to be understood that the particularity of the following description of the invention is not to supersede the generality of the preceding description of the invention.

EXAMPLES

Example 1: Night Cream

TABLE 1

Night Cream Formulation

| Phase | Added % w/w | Raw Materials | INCI Name |
|---|---|---|---|
| A | 64.29 | Purified Water | aqua |
| A | 0.01 | Disodium EDTA | disodium EDTA |
| A | 1.00 | Mikrokill ® ECT | benzyl alcohol, salicylic acid, glycerin, sorbic acid |
| B | 0.90 | Carrageenan Lambda | chondrus crispus |
| B | 0.30 | Xanthan 200 | xanthan gum |
| C | 5.40 | Cosmowax D | cetearyl alcohol and ceteareth-20 |
| C | 4.00 | DC 200 Fluid 350 CST | Dimethicone |
| C | 3.00 | DC 9040 Silicone Elastomer Blend | cyclopentasiloxane (and) dimethicone crosspolymer |
| C | 2.00 | Stearic acid | stearic acid |
| C | 1.00 | Crodamol IPM-LQ-(SG) | isopropyl myristate |
| D | 3.00 | Cutipure CLR ™ | Water, *Taraktogenos kurzii* seed oil, *Nigella sativa* seed oil, *Leptospermum scoparium* branch/leaf oil, potassium lauroyl wheat amino acids, palm glycerides, capryloyl glycine, *Magnolia grandiflora* bark extract |
| D | 2.00 | Hylasome ® EG10 | Sodium Hyaluronate Crosspolymer |
| D | 1.00 | Azeloglicina ® | potassium azeloyl diglycinate |
| D | 1.00 | Lipobelle Soyaglycone | lecithin (and) soy isoflavones (and) polysorbate 80 (and) alcohol (and) water |
| D | 1.00 | Metabiotics ™ Resveratrol | *Pichia pastoris*/resveratrol ferment extract |
| D | 0.50 | NanoMax | lecithin (and) ascorbyl tetraiso-palmitate (and) caprylic/capric triglycerides (and) tocopherol acetate (and) tocopherol (and) ubiquinone (and) diisopropyl adipate (and) glycerin (and) alcohol (and) water |
| E | 4.00 | Glycerin 99.5% BP/EP | glycerin |
| E | 3.00 | Vitamin C powder | sodium ascorbyl phosphate |
| E | 1.00 | Salicylic acid BP | salicylic acid |
| F | 1.50 | Purified Water | aqua |
| G | 0.10 | Vitamin A - Retinol 15D | caprylic/capric triglyceride (and) retinol |
|  | q.s. | Lactic acid 88% | lactic acid, water |
|  | 100.00 | Total |  |

Compounding Procedure:

All ingredients from phase A were added together, and stirred until combined. The mixture was heated to 75° C. The ingredients from phase B were then sifted into the phase A mixture and stirred until thoroughly hydrated.

The phase C ingredients were added together and stirred at 75° C. until the ingredients had melted and thoroughly blended.

With both phase A/B and phase C at 75° C., phase C was added to phase A/B and the mixture emulsified. This mixture was then allowed to cool to 35° C. under constant low shear. The phase D ingredients were next added to phase A/B/C, and stirring was continued under low shear until the mixture was homogenous.

The phase E ingredients were added and then stirred well to provide a smooth paste. Purified water (phase F) was then added to phase E and mixed until homogenous.

Phase E/F was next added to phase A/B/C/D and stirring was continued under low shear until the mixture was homogenous. Vitamin A-Retinol 15D (phase G) was then added to phase A/B/C/D/E/F and stirring was again continued under low shear until the mixture was homogenous. Lactic acid was then added to adjust the pH to between 5.5 and 6.5. The mixture was then allowed to cool below 25° C. before it was poured off.

Example 2: Active Gel

TABLE 2

Active Gel Formulation

| Phase | Added % w/w | Raw Materials | INCI Name |
|---|---|---|---|
| A | 86.70 | Purified Water | aqua |
| A | 1.00 | Mikrokill ® ECT | benzyl alcohol, salicylic acid, glycerin, sorbic acid |
| A | 0.20 | Disodium EDTA | disodium EDTA |
| B | 0.80 | Carbopol ® 940 | Carbomer |
| C | 4.00 | Glycerin 99.5% BP/EP | glycerin |
| C | 1.00 | Metabiotics ™ Resveratrol | *Pichia pastoris*/resveratrol ferment extract |
| C | 1.00 | Salicylic acid BP | salicylic acid |
| C | 0.10 | Azeloglicina ® | potassium azeloyl diglycinate |
| C | 0.10 | Hylasome ® EG 10 | Sodium Hyaluronate Crosspolymer |
| D | 4.00 | NaOH soln 10% | Water, sodium hydroxide |
| E | 0.80 | polysorbate 20 | polysorbate-20 |
| E | 0.30 | Cutipure CLR ™ | Water, *Taraktogenos kurzii* seed oil, *Nigella sativa* seed oil, *Leptospermum scoparium* branch/leaf oil, potassium lauroyl wheat amino acids, palm glycerides, capryloyl glycine, *Magnolia grandiflora* bark extract |
|  | 100.00 | Total |  |

Compounding Procedure:

All ingredients from phase A were added together and stirred well until combined. Carbopol 940 (phase B) was then added to the phase A mixture and stirred until the carbopol was transparent.

The phase C ingredients were added together and mixed to make a slurry. Following this, phase C was added to phase A/B and the mixture stirred until homogenous. NaOH (phase D) was then added to phase A/B/C and stirred well until thoroughly hydrated.

The phase E ingredients were added together and mixed well to disperse Cutipure in the polysorbate-20. Phase E was then added slowly to phase A/B/C/D and stirred well until the mixture was homogenous. The pH of the resultant mixture was then adjusted to a pH between 5.0 and 6.0.

pH of the mixture was then adjusted with lactic acid (approximately 0.1%) to between 5.5 and 6.5.

Example 3: Serum

TABLE 3

Serum Formulation

| Phase | Added % w/w | Raw Materials | INCI Name |
|---|---|---|---|
| A | 65.10 | water | aqua |
| A | 1.00 | Euxyl ® PE 9010 | phenoxyethanol (and) ethylhexylglycerin |
| B | 4.00 | glycerin | glycerin |
| B | 0.40 | Xanthan 200 | xanthan gum |
| C | 4.00 | Crodamol IPM-LQ-(SG) | isopropyl myristate |
| C | 1.50 | Eumulgin ® SG | sodium stearoyl glutamate |
| C | 4.00 | Emulgade ® PL68/50 | cetearyl glucoside, cetearyl alcohol |
| C | 3.00 | DC 9040 Silicone Elastomer Blend | cyclopentasiloxane (and) dimethicone crosspolymer |
| D | 6.00 | Glycerin 99.5% BP/EP | glycerin |
| D | 3.00 | Sodium Ascorbyl Phosphate | sodium ascorbyl phosphate |
| E | 3.00 | Cutipure CLR ™ | Water, *Taraktogenos kurzii* seed oil, *Nigella sativa* seed oil, *Leptospermum scoparium* branch/leaf oil, potassium lauroyl wheat amino acids, palm glycerides, capryloyl glycine, *Magnolia grandiflora* bark extract |
| E | 2.00 | Hylasome ® EG10 | sodium hyaluronate crosspolymer |
| E | 1.00 | Azeloglicina ® | potassium azeloyl diglycinate |
| E | 1.00 | Metabiotics ™ Resveratrol | *Pichia pastoris*/resveratrol ferment extract |
| E | 0.50 | Lipobelle Soyaglycone | lecithin (and) soy isoflavones (and) polysorbate 80 (and) alcohol (and) water |
| E | 0.50 | NanoMax | lecithin (and) ascorbyl tetraisopalmitate (and) caprylic/capric triglycerides (and) tocopherol acetate (and) tocopherol (and) ubiquinone (and) diisopropyl adipate (and) glycerin (and) alcohol (and) water |
| | q.s. | Lactic acid 88% | lactic acid, water |
| | 100.00 | Total | |

Compounding Procedure

The phase A ingredients were added together and stirred until combined. The mixture was heated to 75° C.

The phase B ingredients were added together to disperse the xanthan gum in the glycerin. Phase B was then added to phase A and the mixture stirred until thoroughly hydrated. During this step, the temperature was maintained at 75° C.

The phase C ingredients were added together, and stirred at 75° C. until the ingredients had melted and thoroughly blended.

With both phase C and phase A/B at 75° C., phase C was added to phase A/B and the mixture emulsified. This mixture was then allowed to cool to 35° C. under constant low shear.

The phase D ingredients were added together and stirred well to thoroughly disperse sodium ascorbyl phosphate in the glycerin. The phase E ingredients were then added to phase D and stirred well until the mixture was homogenous.

Phase D/E was then added to phase A/B/C and again stirred thoroughly until the mixture was homogenous. The

Example 4: Day Cream

TABLE 4

Day Cream Formulation

| Phase | Added % w/w | Raw Materials | INCI Name |
|---|---|---|---|
| A | 51.40 | Purified Water | aqua |
| A | 4.00 | Glycerin 99.5% BP/EP | glycerin |
| A | 0.70 | Euxyl ® PE 9010 | phenoxyethanol (and) ethylhexylglycerin |
| B | 0.60 | Carrageenan Lambda | chondrus crispus |
| B | 0.30 | Xanthan 200 | xanthan gum |
| C | 20.00 | Solaveil ™ CZ-300 | zinc oxide (and) caprylic/capric triglyceride (and) polyhydroxystearic acid (and) isostearic acid |
| C | 2.00 | UV Titan M161 | titanium dioxide (and) stearic acid (and) alumina |
| D | 6.00 | Crodamol IPM-LQ-(SG) | isopropyl myristate |
| D | 5.50 | Cosmowax D | cetearyl alcohol and ceteareth-20 |
| D | 3.00 | DC 200 Fluid 100 CST | Dimethicone |
| E | 3.00 | Cutipure CLR ™ | Water, *Taraktogenos kurzii* seed oil, *Nigella sativa* seed oil, *Leptospermum scoparium* branch/leaf oil, potassium lauroyl wheat amino acids, palm glycerides, capryloyl glycine, *Magnolia grandiflora* bark extract |
| E | 2.00 | Hylasome ® EG10 | Sodium Hyaluronate Crosspolymer |
| E | 1.00 | Metabiotics ™ Resveratrol | *Pichia pastoris*/resveratrol ferment extract |
| E | 0.50 | NanoMax | lecithin (and) ascorbyl tetraisopalmitate (and) caprylic/capric triglycerides (and) tocopherol acetate (and) tocopherol (and) ubiquinone (and) diisopropyl adipate (and) glycerin (and) alcohol (and) water |
| | 100.00 | Total | |

Compounding Procedure

All ingredients from phase A were added together and stirred until combined. This mixture was heated to 75° C. The phase B ingredients were then sifted into phase A and the mixture stirred until thoroughly hydrated.

The phase C ingredients were added together and stirred well to form a slurry. The phase D ingredients were then added to phase C and this was stirred well at 75° C. to melt and thoroughly blend the ingredients.

With both phase C/D and phase A/B at 75° C., phase C/D was added to phase A/B and the mixture emulsified. This mixture was then allowed to cool to 35° C. under constant low shear. Phase E ingredients were next added and the stirring was continued under low shear until the mixture was homogenous. The pH of the mixture was then adjusted to between 6.5 to 7.5 and the mixture allowed to cool to below 25° C. before pouring off.

Example 5: Face Wash

TABLE 5

Face Wash Formulation

| Phase | Added % w/w | Raw Materials | INCI Name |
|---|---|---|---|
| A | 40.30 | water | aqua |
| A | 1.00 | Mikrokill ® ECT | benzyl alcohol, salicylic acid, glycerin, sorbic acid |
| A | 0.10 | Disodium EDTA | disodium EDTA |
| B | 30.00 | Genagen ® CAB | cocoamidopropylbetaine |
| C | 12.00 | Medialan ® LD | Sodium lauroyl sarcosinate |
| D | 4.00 | Glycerin 99.5% BP/EP | glycerin |
| D | 0.80 | Carrageenan lambda | chondrus crispus |
| D | 0.60 | Xanthan 200 | xanthan gum |
| E | 5.50 | Glycerin 99.5% BP/EP | glycerin |
| E | 2.00 | Salicylic acid BP | salicylic acid |
| E | 2.00 | Polyethylene powder | polyethylene |
| E | 1.00 | Florabeads ® Maize | Jojoba esters (and) CI77492 |
| E | 0.30 | Hylasome ® EG10 | sodium hyaluronate crosspolymer |
| E | 0.30 | Sodium Ascorbyl Phosphate | sodium ascorbyl phosphate |
| E | 0.10 | Azeloglicina ® | potassium azeloyl diglycinate |
| | q.s. | NaOH soln 10% | aqua (and) sodium hydroxide |
| | 100.00 | Total | |

Compounding Procedure

All ingredients from phase A were added together and the mixture was stirred until combined. Genagen® CAB (phase B) was then added to phase A and the mixture stirred until homogenous. Medialan® LD (phase C) was next added to phase A/B and the mixture again stirred until it was homogenous.

Carrageenan lambda and Xanthan 200 were dispersed in the glycerin to form a slurry (phase D). Phase D was then added to phase A/B/C and the mixture stirred until thoroughly hydrated.

The phase E ingredients were then added together and the mixture was stirred well to form a smooth paste. Phase E was next added to phase A/B/C/D and the mixture stirred under low shear until homogenous. The pH of the mixture was then adjusted to between 5.5 and 6.5 with NaOH.

Example 6: Skin Tests

To test the effect of sodium hyaluronate crosspolymer in the formulation, skin tests were performed. The formulations tested were the Serum Formulation described in Example 3 including sodium hyaluronate crosspolymer (WH or W), and a Serum Formulation as described in Example 3 but which did not include sodium hyaluronate crosspolymer (NH or N). Tests were performed by the Australian Photobiology Testing Facility Pty Limited.

Subject Selection

Female test subjects were selected for Acne (comedones, pustules and pimples) on both sides of the face (minimum of three per side of face). Test subjects were selected to be non-smokers, occasional non-drinkers (0-4 units of alcohol per week), not taking medication for skin condition, not pregnant or trying to fall pregnant. Test subjects were also selected for pale, minimally sun exposed back skin (preferentially skin types I and II and III) free of confounding blemishes. Medical history forms were completed (including dietary information which has been found to be important for estimating expected responses to UV exposure).

Eight subjects of between 18 and 39 years of age were selected according to the selection criteria. Some subjects, as shown in Tables 6 and 7, had allergies or were on medication.

TABLE 6

Subjects, their gender and allergies

| SUBJECT | SEX | ALLERGY |
|---|---|---|
| 1 | F | Cats, dogs, pollen and mould |
| 2 | F | Dairy, Penicillin, Codeine |
| 3 | F | Stematil |

TABLE 7

Subjects, their gender and medication

| SUBJECT | SEX | MEDICATION |
|---|---|---|
| 4 | F | Oral Contraceptive Pill |
| 2 | F | Oral Contraceptive Pill |

Methods

The test materials arrived in plain coded containers.

All eight test subjects undertook an Anti-Inflammatory Test on both products prior to the start of the study. The Anti-inflammatory Test was repeated at the end of the study.

Anti-Inflammatory

Summary of Protocol

On day one the subject received a series of UV exposures, with one second increments between each exposure, on unprotected skin. The minimal erythemal dose (MED) of the subject was determined 16-24 hours later.

On day two, all day one responses were observed, scored and photographed. Using the subjects MED as the mean exposure dose in a series of exposures, four further doses were next calculated with ×1.25 increments between them: three below the MED, one exposure at the MED, and one above the MED. The test products were applied to the skin at the rate of 4 mg/cm$^2$ in two applications, one immediately following the series of irradiations, and one four to five hours later.

On day three, all day two responses were observed, scored and photographed. Scoring was performed by according the value of 1.0 to the MED as defined above, and using increments of 0.25 to grade all responses either higher or lower than 1.0.

Light Source-Solar Simulator, and Radiometry

The light source used was a 150 W, 16S single port solar simulator (Solar Light Co., Phil., US) incorporating collimating and focusing lenses and Schott glass filters which attenuate UV emission to approximate the sunlight spectrum. This light source has been measured by the Commonwealth Scientific and Industrial Research Organisation (CSIRO) National Measurements Laboratory, Division of Applied Physics, using a computer controlled McPherson triple grating monochromator, and its emission spectrum falls within the limits set in the Australian Standard. The radiometer used to check, monitor and adjust the solar simulator emission intensity is an IL 1700 Research Radiometer with the appropriate detectors, filters, and cosine correcting diffuser. This instrument is capable of measuring UVB (280-315 nm), UVA (316-400 nm), and total UV, and calibrated by the CSIRO National Measurements Laboratory, Division of Applied Physics to the particular source it is measuring. The light source is also measured every week using a Stellarnet Spectroradiometer.

The beam intensity is measured at the focal point of the optical system which is where the skin rests, at the correct distance, against a wedge of metal plate (the Spacer) from the widest portion of which a 40 mm aperture had been cut. This adjustable Spacer ensures that the skin which abuts it is at the same distance as the focal point of the beam(s) emitted (direct or reflected light). The radiometer detector head fits the Spacer exactly.

The Spacer includes a ring, which defines a circumference the centre of which is also the centre of the 10 mm beam of UV irradiance. A further section is cut from the supplied 3 mm ring to mitigate the possibility, of disturbing the applied formulation when moving the ring in a fixed focal length position across the prescribed area of the back. Removing a section retains the necessary focal point distance and circumferential location of the beam, but prevents any disturbance of the formulation applied to the skin, as it is moved from one irradiation/exposure sub-site to the next.

Subject Orientation and Stabilisation

Both the specially designed chair upon which the subject sits upright during exposure, and the light source itself, are moveable in such a way as to ensure the correct orientation of the curves of the back skin to the incident light. A device has also been engineered which enables the continuous monitoring and correction by the test subject and test operator of the precise orientation and positioning of the subsite exposed to UV, and within 1 mm of travel from the focal point distance. This device alerts both the operator and the test subject by the rapid sounding of different tones when, and in which direction to move, or be moved (slightly), to reassume correct positioning and UV exposure intensity.

Minimal Erythemal Dose (MED) Evaluation

Skin erythema (reddening) was evaluated by visual observation and comparison under constant tungsten illumination of the test area, and under conditions where room lighting has been designed for red colour rendering. The colour acuity of the test operators has been evaluated by the Farnsworth Munsel Test, and the US Colour Test, and found to be in the top 1%. The operators have over fifteen (15) years experience with skin response colour evaluation and comparison.

Response sub-sites were evaluated and scored by visual comparison. The value of 1.0 was accorded to the MED as defined above. Responses of greater intensities were accorded values of 1.25-2.0, and of lesser intensities 0.25-0.75. No response was 0.0.

Test Site Area

The dorsum or back area was the only area used in this study. A test site area was outlined for determining the subjects Minimal Erythemal Dose (MED) on unprotected skin (control site). This site was carefully chosen for its representative (usually mid-dorsum) features with respect to i) any gradation of pigmentation usually seen on the backs of test subjects, and ii) with respect to test sites to be delineated for exposures after application of the test materials. The subject's MED is the time/dose of exposure that produces the minimal perceptible erythema, observed 16 to 24 hours post exposure. The MED response sub-site is that sub-site showing a well circumscribed, full beam size circle, flanked on one side by a no response sub-site and on the other by a greater than response sub-site.

Test Sub-Site Area

The area to be exposed was on the back between the belt line and the scapulae (shoulder blade) and lateral midline. The test site areas were horizontal (latitudinal on either side of the spine). Each test site area for exposure after applying a test product was 30 cm square. These test sites were spot-outlined with a waterproof pen while the subject was in an upright position. Each site was divided into five test sub-site areas that were at least 1 cm square with >1 cm between sub-sites. All subject test sites were photographed with a digital camera.

Application of Test Material

The products were applied to the skin at the rate of 4 $mg/cm^2$ in two applications, one immediately following the series of irradiations, and one four to five hours later. The products were all rubbed in well.

Acne Count

Female test subjects were selected for Acne (comedones, pustules and pimples) and a minimum of three per side of face. Face maps of acne and counts of acne were taken at t-0, t-4 and t-8 weeks. All subjects were photographed by a professional photographer at t-0 and t-8 weeks.

Sebum Measurements

On day three of the Anti-inflammatory Study and after a skin settling period of 15 minutes Sebum measurements were taken at t-0. Sebum measurements were also taken at t-4 and t-8 weeks. Sebum production was measured at eighteen facial locations and recorded. These locations included the left, centre and right of forehead; the left, middle and bottom of both sides of both the left and right cheeks; and the left, middle and right area below the lip. The instrument used for measuring sebum production was a Sebumeter SM 810/Corneometer CM 825/Skin-pH-Meter PH 900, made by Courage+Khazaki Electronic GmbH, Mathias-Bruggen-Str. 91D-50829 Koln, Germany.

Product Application

Subjects were randomly divided into two groups of four and assigned either the NH or WH product. All subjects were instructed to apply to their face a specific amount of product twice a day. For this a measuring spoon was issued to each subject and each subject was shown how much product should be used. Subjects were instructed to use the test product twice a day, morning and evening, on their whole face and to rub the product well into the skin. The products were weighed at t-0, t-4 and t-8 weeks to ensure compliance to instructions.

Results

Anti-Inflammatory

Figure 2:
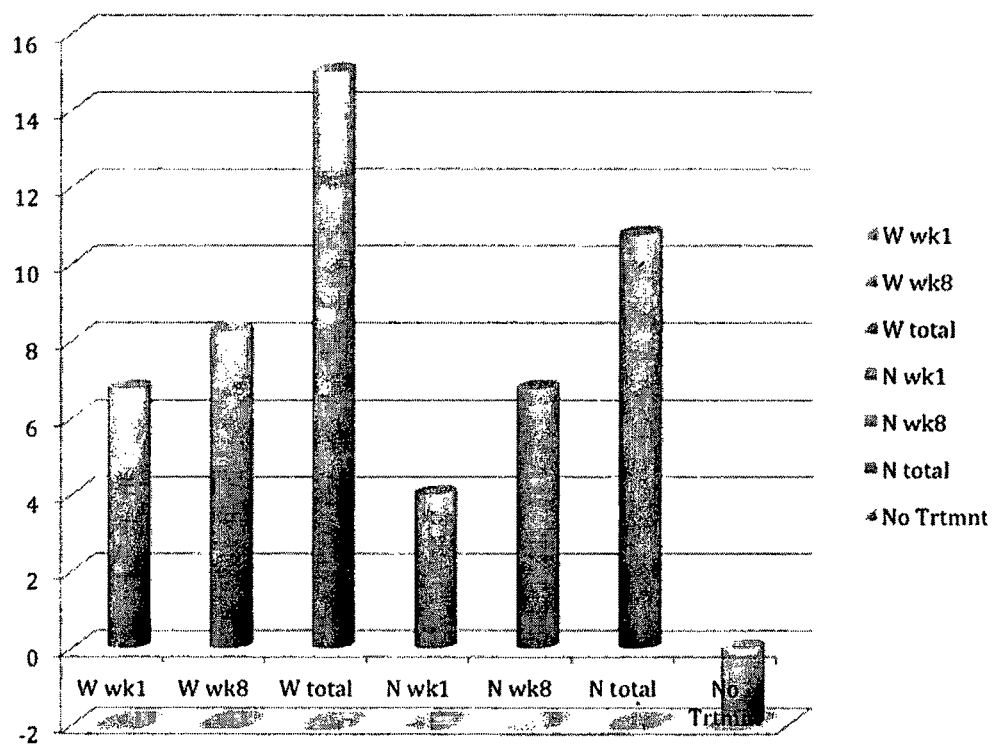
FIG. 2 shows the anti-inflammatory effect of the N (a formulation without sodium hyaluronate crosspolymer) and W (a formulation with sodium hyaluronate crosspolymer) formulations as a function of the change in Minimal Erythemal Dose (MED) in seconds.

FIG. 1 shows the anti-inflammatory effect of the N and W formulations as an average percentage change in the reduction in skin responsiveness. The average percentage change illustrated in FIG. 1 was derived from the Score data. FIG. 2 shows the anti-inflammatory effect of the formulations as a function of the change in Minimal Erythemal Dose (MED) in seconds. As described in the Methods section the MED is the dose (in seconds) identified as that which produces a minimally perceptible reddening of the skin. The dose necessary to produce the MED following application of the W and N formulations was higher against the baseline indicating a protective effect conferred, where the W product appeared to be more effective. An anti-inflammatory effect was clearly observed with the W and N formulations, and a greater effect was observed with the W product.

Sebum Measurement

Figure 3A:
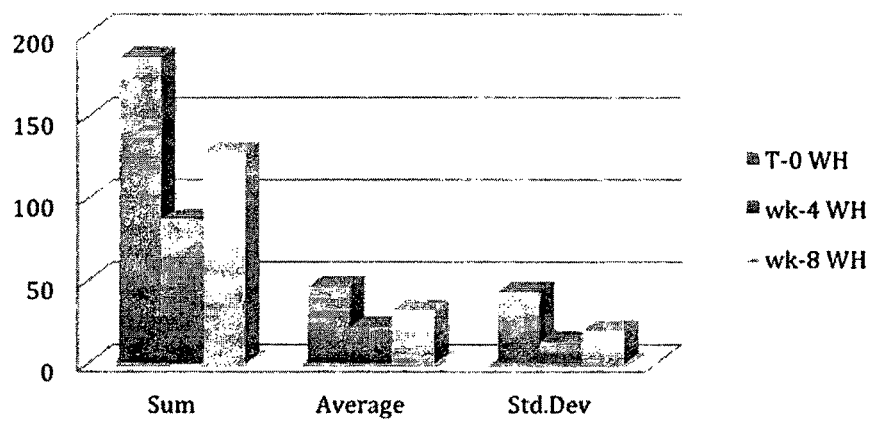
FIG. 3A) and the NH formulation (without sodium hyaluronate crosspolymer.
Figure 3B:
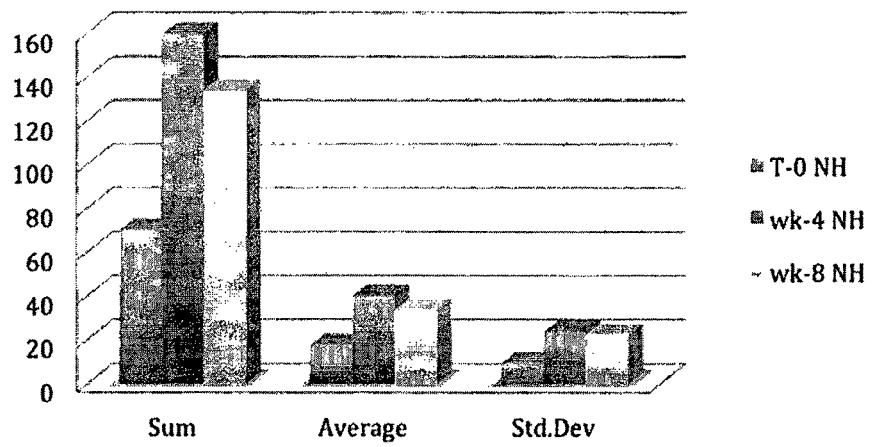
FIG. 3B) on sebum levels.

The WH formulation (FIG. 3A) reduces sebum levels to a greater degree than the NH formulation (FIG. 3B).

Acne Count

All but one of the test subjects had some reduction of acne at the eight week time point. The acne count overall is shown in Table 8.

TABLE 8

Acne Count with absolute numbers

|  | T-0 | wk-4 | wk-8 |
|---|---|---|---|
| NH | | | |
| Sum | 84 | 65 | 49 |
| Average | 21 | 16 | 12 |
| Std. Dev | 12 | 7 | 5 |
| WH | | | |
| Sum | 59 | 39 | 55 |
| Average | 15 | 10 | 14 |
| Std. Dev | 2 | 5 | 7 |

Product Usage

Table 9 shows the product usage data. Subject F used more than the other test subjects but this had no effect on the parameters measured. The average and standard deviations indicate that compliance was reasonable.

TABLE 9

Product usage data

| Subject/Product | Useage wk 4 gms | Useage wk 8 gms |
|---|---|---|
| E/NH | 20.034 | 18.003 |
| H/NH | 20.489 | 25.899 |
| F/NH | 16.946 | 42.437 |
| G/NH | 20.311 | 15.41 |
| A/WH | 15.478 | 19.871 |
| B/WH | 23.831 | 29.76 |
| C/WH | 13.514 | 17.289 |
| D/WH | 10.533 | 13.474 |
| Average | 17.642 | 22.767 |
| Std. Dev | 4.342 | 9.615 |

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The claims defining the invention are as follows:

1. A cosmetic or pharmaceutical formulation for treating or preventing one or more of a condition involving blocked sebaceous glands, an inflammatory skin condition, a microbial skin infection, dermal oxidation damage and pigmentation, the formulation comprising:
   (i) a hyaluronate crosspolymer or a salt thereof in an amount of 0.05% to 4% w/w; and
   (ii) 0.2% to 4% w/w of a mixture consisting of comprising black cumin seed oil, chaulmoogra oil, magnolia bark extract and Manuka oil.

2. The formulation of claim 1, further comprising one or more of:
   (a) azelaic acid or a salt or ester thereof; and
   (b) resveratrol or a derivative thereof.

3. The formulation of claim 2, comprising:
   (a) azelaic acid or a salt or ester thereof; and
   (b) resveratrol or a derivative thereof.

4. The formulation of claim 1, wherein the formulation comprises the hyaluronate crosspolymer or a salt thereof in an amount of 0.1 to 2% w/w.

5. The formulation of claim 1, wherein the mixture includes one or more of thymoquinone, 5'-methoxyhydnocarpin, hydnocarpic acid, chaulmoogric acid, gorlic acid, honokiol, magnolol, flavesone, leptospermone and isoleptospermone.

6. The formulation of claim 2, wherein the azelaic acid or a salt or ester thereof is a mono- or di-ester of azelaic acid with an amino acid or a salt thereof.

7. The formulation of claim 6, wherein the mono- or di-ester of azelaic acid is azeloyl diglycinate or a salt thereof.

8. The formulation of claim 2, wherein the formulation comprises azelaic acid or a salt or ester thereof in an amount of less than 5% w/w.

9. The formulation of claim 2, wherein the resveratrol or a derivative thereof is a derivative of resveratrol.

10. The formulation of claim 9, wherein the derivative of resveratrol is a product from an enzymatic treatment of resveratrol.

11. The formulation of claim 10, wherein the derivative of resveratrol is an extract produced by fermentation of resveratrol.

12. The formulation of claim 2, wherein the formulation comprises resveratrol or a derivative thereof in an amount of less than 5% w/w.

13. The formulation of claim 1, wherein the formulation further includes one or more agents that stimulate collagen production.

14. The formulation of claim 13, wherein the one or more agents that stimulate collagen production are selected from one or more of: a retinoid, an isoflavone or a substituted derivative thereof and salicylic acid or a salt or derivative thereof.

15. The formulation of claim 1, wherein the formulation further comprises one or more antioxidants.

16. The formulation of claim 15, wherein the one or more antioxidants are selected from: ascorbic acid or a salt or derivative thereof, tocopherol or a derivative thereof, ubiquinone or a derivative thereof, lactobionic acid or a salt or derivative thereof, gluconolactone or a derivative thereof and maltobionic acid or a salt or derivative thereof.

17. A method of treating or preventing one or more of a condition involving blocked sebaceous glands, an inflammatory skin condition, a microbial skin infection, dermal oxidation damage and pigmentation, comprising administering to a subject in need thereof an effective amount of the formulation of claim 1.

18. The method of claim 17, wherein the microbial skin infection is a bacterial infection.

19. A method of promoting collagen production in a dermal matrix or regulating cellular turnover, comprising administering to a subject in need thereof an effective amount of the formulation of claim 1.

* * * * *